US010632326B2

(12) United States Patent
Zhang et al.

(10) Patent No.: US 10,632,326 B2
(45) Date of Patent: Apr. 28, 2020

(54) SYSTEM AND METHOD FOR RADIATION TREATMENT OPTIMIZED FOR NON-COPLANAR DELIVERY

(71) Applicant: Washington University, St. Louis, MO (US)

(72) Inventors: Tiezhi Zhang, St. Louis, MO (US); Sasa Mutic, St. Louis, MO (US)

(73) Assignee: WASHINGTON UNIVERSITY, St. Louis, MO (US)

(*) Notice: Subject to any disclaimer, the term of this patent is extended or adjusted under 35 U.S.C. 154(b) by 59 days.

(21) Appl. No.: 16/063,034

(22) PCT Filed: Dec. 16, 2016

(86) PCT No.: PCT/US2016/067323
§ 371 (c)(1),
(2) Date: Jun. 15, 2018

(87) PCT Pub. No.: WO2017/106746
PCT Pub. Date: Jun. 22, 2017

(65) Prior Publication Data
US 2018/0361172 A1 Dec. 20, 2018

Related U.S. Application Data

(60) Provisional application No. 62/269,238, filed on Dec. 18, 2015.

(51) Int. Cl.
*A61N 5/10* (2006.01)
*A61B 6/06* (2006.01)
*A61B 6/03* (2006.01)

(52) U.S. Cl.
CPC ......... *A61N 5/1047* (2013.01); *A61N 5/1028* (2013.01); *A61N 5/1049* (2013.01);
(Continued)

(58) Field of Classification Search
None
See application file for complete search history.

(56) References Cited

U.S. PATENT DOCUMENTS 4,980,904 A 12/1990 Sones et al.
6,459,769 B1 10/2002 Cosman
(Continued)

OTHER PUBLICATIONS

International Preliminary Report on Patentability (Chapter I) for PCT/US2016/067323 dated Jun. 28, 2018.
(Continued)

*Primary Examiner* — Hoon K Song
(74) *Attorney, Agent, or Firm* — Thompson Coburn LLP

(57) ABSTRACT

A system or method for radiation treatment optimized for non-coplanar delivery, which includes a first collimator affixed to a gantry and a second collimator movably attached to the gantry to provide the second collimator a translation movement out of a gantry rotation plane. The system or method also includes a third collimator configured to collimate the beam in a direction of a target in the patient's body. The beam collimated by the third collimator is configured to follow the target during treatment. A method of performing rotation setup correction by rotating the treatment beam, without rotating the patient.

17 Claims, 10 Drawing Sheets

(52) U.S. Cl.
CPC ............ *A61N 5/1082* (2013.01); *A61B 6/032* (2013.01); *A61B 6/06* (2013.01); *A61N 5/1065* (2013.01); *A61N 2005/1054* (2013.01)

(56) References Cited

U.S. PATENT DOCUMENTS

| | | |
|---|---|---|
| 6,969,194 B1 | 11/2005 | Nafstadius |
| 8,536,547 B2 | 9/2013 | Maurer, Jr. et al. |
| 2003/0076927 A1 | 4/2003 | Nakashima et al. |
| 2012/0163531 A1 | 6/2012 | Zhang et al. |
| 2018/0272155 A1* | 9/2018 | Thieme ................ A61B 6/4241 |
| 2018/0345042 A1* | 12/2018 | Voronenko ........... A61N 5/1067 |
| 2019/0209863 A1* | 7/2019 | Ollila ................... A61N 5/1031 |
| 2019/0247676 A1* | 8/2019 | Peltola ................. A61N 5/1047 |

OTHER PUBLICATIONS

International Search Report and Written Opinion for PCT/US2016/067323 dated Apr. 24, 2017.

Kamino et al., Development of a Four-Dimensional Image-Guided Radiotherapy System with a Gimbaled X-Ray Head, Int J. Radiat Oncol Biol Phys. Sep. 1, 2006; 66(1): 271-8.

Yue et al., A Method to Implement Full Six-Degree Target Shift Corrections for Rigid Body in Image-guided Radiotherapy, Medical Physics 33, 21-31 (2006).

\* cited by examiner

SYSTEM AND METHOD FOR RADIATION TREATMENT OPTIMIZED FOR NON-COPLANAR DELIVERY

RELATED APPLICATION DATA

The present application is a U.S. National Phase Application of PCT/US2016/067323, filed on Dec. 16, 2016, which claims the benefit of U.S. Provisional Patent Application Ser. No. 62/269,238, filed on Dec. 18, 2015, the disclosures of which are both incorporated herein by their entireties.

STATEMENT REGARDING FEDERALLY SPONSORED RESEARCH OR DEVELOPMENT

None.

BACKGROUND OF THE INVENTION

Field of the Invention

This invention relates generally to a radiation treatment system, more specifically, to a radiation treatment system for optimizing non-coplanar delivery without a gimbal head and a method to correct rotational setup error without using six-degree robotic couch.

General Background Technology

The goal of radiation treatment is to deliver prescribed radiation dose to a target while avoiding overdose to surrounding normal tissues and organs. A radiation treatment plan comprises multiple beams with different gantry angles in order to spread an entrance and exit dose to a larger volume. In some clinical situations, coplanar dose delivery may be insufficient and non-coplanar beams are used to spread a radiation dose to an even larger area. The concept of 4π treatment planning is to deliver radiation beams from as many spatial angles as possible. Regular LINACs deliver non-coplanar beams by rotating a couch and gantry together. This approach is not efficient and susceptible to collision between the machine gantry, couch, and the patient. Dosimetrists and physicists are careful in choosing machine orientation in treatment planning to ensure deliverability.

FIG. 1 shows an exemplary embodiment of a conventional LINAC head 110, e.g., c-band. The LINAC head 110 shown in FIG. 1 comprises an electron beam from an electron gun 90, a tungsten target 115, radiation treatment beam 116, a primary collimator 120 which defines a maximum field size, a monitor chamber 130 which measures the output of the radiation beam that passes through a flattening filter 125, a secondary collimator 140, and a multi-leaf collimator (MLC) 160 which defines a field shape according to a target. In this embodiment, all of the collimators 120, 140, and 160 are affixed to the combination of the electron gun 90, the primary collimator 120 and the target 115, and thus, are configured to rotate or move as a whole in order to align the radiation treatment beam with the isocenter of a patient.

Radiation treatment systems using the conventional LINAC head provide certain disadvantages as the whole LINAC head must be controlled to move in order to deliver non-coplanar beam. One such system is CyberKnife®, where CyberKnife® is a federally registered trademark of Accuray Incorporated, a Delaware Corporation, having a place of business at 1310 Chesapeake Terrace, Sunnyvale Calif. 94089. CyberKnife® is a radiation treatment machine designed especially for non-coplanar beam delivery. CyberKnife® comprises a compact linear accelerator mounted on a robotic arm, which can be used for both intracranial and extracranial radiosurgery. Quality assurance is important for CyberKnife® due to its large number of motion freedoms. Moreover, it is difficult to integrate volumetric imaging modality such as cone beam CT (CBCT) on a CyberKnife® machine. CyberKnife® can only employ stereoscopic imaging, which comprises orthogonal x-ray planar imaging, which is not as accurate as 3-D volumetric CT imaging. Current CyberKnife® systems can only deliver beams from above due to the size of LINAC head, which impose a major constraint in treatment planning.

Another exemplary system using the conventional LINAC head is described in U.S. Pat. No. 6,969,194 (to Näfstadius) and U.S. Pat. No. 8,536,547 (to Maurer, Jr. et al.). Näfstadius discloses a few designs of a radiation treatment machine that can rotate in a plane perpendicular to a gantry's rotation plane, for example, using a gimbal structure. Maurer discloses a design with a tilt angle. It also discloses a method to turn a LINAC head and tracking a patient at different longitudinal position. All of these systems and methods require moving and/or rotating a treatment head, which includes a LINAC with beam collimation. The size and weight of the treatment head (i.e., LINAC head) make the design of such system very challenging in an engineering point of view.

Another exemplary system using the conventional LINAC head is described in Kamino et al. (*Development of a Four-Dimensional Image-Guided Radiotherapy System with a Gimbaled X-Ray Head*, Int J Radiat Oncol Biol Phys. 2006 Sep. 1; 66(1):271-8. Epub 2006 Jul. 3).

The present invention is directed to overcoming one or more of the problems set forth above.

SUMMARY OF THE INVENTION

In one aspect of the invention, a system for radiation treatment, said system comprising: a gantry configured to rotate around a body of a patient positioned along with a longitudinal axis; a radiation treatment source affixed to said gantry, wherein said x-ray source is configured to emit the x-ray treatment beam in a direction that is transverse to said longitudinal axis; a first collimator affixed to said gantry, wherein said first collimator is configured to collimate the x-ray treatment beam emitted from said radiation treatment source; and a second collimator movably attached to said gantry, wherein said second collimator is configured to further collimate the x-ray treatment beam collimated by said first collimator and move out of a gantry rotation plane along said longitudinal axis.

In another aspect of the invention, a system for correcting rotational setup error of radiation treatment, said system comprising: a gantry configured to rotate around a body of a patient positioned along with a longitudinal axis; a radiation treatment source affixed to said gantry, wherein said radiation treatment source is configured to emit the x-ray treatment beam in a direction that is transverse to said longitudinal axis; a collimator configured to collimate the x-ray treatment beam emitted from said radiation treatment source; a couch configured to translate the patient along said longitudinal axis; and a control unit configured to correct rotation setup error of the patient by using at least one of a gantry angle, non-coplanar angle, and collimator angle such that an orientation of the x-ray treatment beam relative to the patient remains unchanged throughout treatment.

In still another aspect of the invention, a method for radiation treatment, said method comprising: rotating a gantry around a body of a patient positioned along with a longitudinal axis; emitting x-ray treatment beam with a radiation treatment source, wherein the x-ray treatment beam is emitted in a direction that is transverse to said longitudinal axis, wherein said x-ray treatment source is affixed to said gantry; collimating the x-ray treatment beam with a first collimator, wherein said first collimator is affixed to said gantry; further collimating the x-ray treatment beam with a second collimator, wherein said second collimator is movably attached to said gantry; and moving said second collimator out of a gantry rotation plane along said longitudinal axis.

In still another aspect of the invention, the method for radiation treatment, wherein the x-ray treatment beam is emitted in a direction that is substantially perpendicular to said longitudinal axis.

In still another aspect of the invention, the method for radiation treatment, said method further comprising: moving said third collimator, wherein said third collimator is a cone collimator, wherein said cone collimator is movably attached to a guiding rail and configured to move along said guiding rail relative to the movement of the patient such that the x-ray treatment beam follows the target while the patient moves along said longitudinal axis.

In still another aspect of the invention, the method for radiation treatment, said method further comprising: moving said third collimator, wherein said third collimator is a multi-leaf collimator comprising a single layer, wherein said multi-leaf collimator is affixed to a rotatable cartridge, wherein said rotatable cartridge is configured to move with said multi-leaf collimator relative to the movement of the patient such that the x-ray treatment beam follows the target while the patient moves along said longitudinal axis.

In still another aspect of the invention, the method for radiation treatment, said method further comprising: moving said third collimator, wherein said third collimator is a multi-leaf collimator comprising a plurality of layers, wherein said multi-leaf collimator is affixed to a non-rotatable cartridge, wherein the x-ray treatment beam is collimated to follow the target while the patient moves along said longitudinal axis.

In still another aspect of the invention, the method for radiation treatment, said method further comprising: translating said non-rotating cartridge out of said gantry rotation plane along said longitudinal axis such that the x-ray treatment beam collimated by said multi-leaf collimator follows the target while the patient moves along said longitudinal axis.

In still another aspect of the invention, the method for radiation treatment, said method further comprising: controlling rotation movement of said third collimator by rotating said third collimator by a plurality of non-coplanar angles relative to said gantry rotation plane.

In still another aspect of the invention, the method for radiation treatment, wherein a radiation field collimated by said first collimator is larger than a radiation field collimated by said second collimator, wherein said radiation field collimated by said second collimator encompasses at least a partial target volume.

In still another aspect of the invention, the method for radiation treatment, wherein said radiation field collimated by said second collimator is larger than a radiation field collimated by said third collimator, wherein said radiation field collimated by said third collimator defines an actual shape of said radiation field collimated by said third collimator.

In still another aspect of the invention, the method for radiation treatment, said method further comprising: moving said patient with a couch along said longitudinal axis.

In still another aspect of the invention, the method for radiation treatment, wherein said x-ray treatment source is one of a linear accelerator (LINAC) and co-60.

In still another aspect of the invention, the method for radiation treatment, wherein said gantry is one of a ring gantry or c-arm gantry.

In still another aspect of the invention, the method for radiation treatment, wherein said cone collimator comprises an iris aperture with a plurality of layers, wherein said layers are configured to move coordinately in order to change an aperture size of said iris aperture at different layer levels such that an edge of each layer follows divergence of the x-ray treatment beam.

In still another aspect of the invention, the method for radiation treatment, wherein said movement of said second collimator comprises one of rotational movement, tilting movement, and translational movement.

Yet another aspect of the present invention is a method for correcting rotational setup error of radiation treatment, said method comprising: rotating a gantry around a body of a patient positioned along with a longitudinal axis; emitting x-ray treatment beam with a radiation treatment source, wherein the x-ray treatment beam is emitted in a direction that is transverse to said longitudinal axis, wherein said x-ray treatment source is affixed to said gantry; collimating the x-ray treatment beam with a collimator; translating the patient with a couch along said longitudinal axis; correcting rotation setup error of the patient by using at least one of a gantry angle, non-coplanar angle, and collimator angle such that an orientation of the x-ray treatment beam relative to the patient remains unchanged throughout treatment.

Yet another aspect of the present invention, the method for correcting rotational setup error of radiation treatment, said method further comprising: translating said collimator out of said gantry rotation plane along said longitudinal axis, wherein said collimator is movably attached to said gantry.

Yet another aspect of the present invention, the method for correcting rotational setup error of radiation treatment, wherein said rotation setup error of the patient by using at non-coplanar angle includes a robotic radiosurgery system in conjunction with a linear accelerator.

These are merely some of the innumerable aspects of the present invention and should not be deemed an all-inclusive listing of the innumerable aspects associated with the present invention. These and other aspects will become apparent to those skilled in the art in light of the following disclosure and accompanying drawings.

BRIEF DESCRIPTION OF THE DRAWINGS

For a better understanding of the present invention, reference may be made to the accompanying drawings in which.

Figure 1:
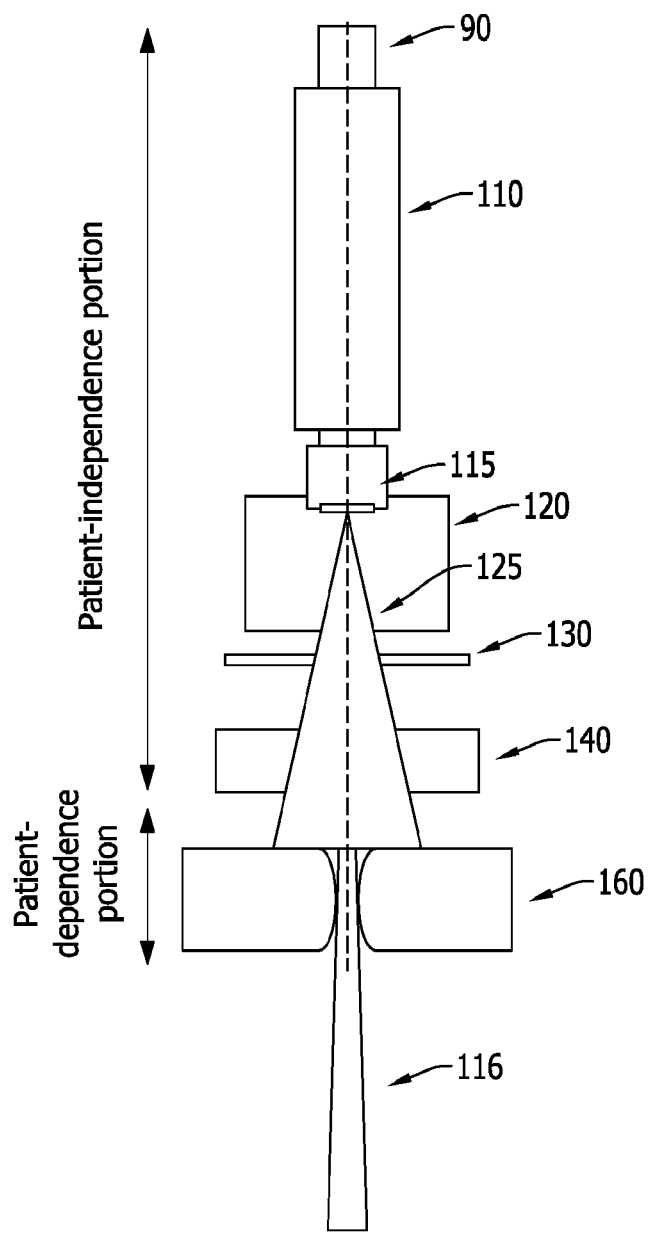
FIG. 1 shows an exemplary embodiment of a conventional LINAC head.

Reference characters in the written specification indicate corresponding items shown throughout the drawing figures.

DETAILED DESCRIPTION OF THE INVENTION

In the following detailed description, numerous exemplary specific details are set forth in order to provide a thorough understanding of the invention. However, it will be understood by those skilled in the art that the present invention may be practiced without these specific details, or with various modifications of the details. In other instances, well know methods, procedures, and components have not been described in detail so as not to obscure the present invention.

In order to overcome the disadvantages found in the prior art previously described above, radiation treatment systems that are capable of delivering non-coplanar beams without a gimbal head and perform full six degree positioning are introduced here. In the proposed systems, a treatment head (i.e., a LINAC head) rotates in a gantry when a patient translates during treatment; however, instead of rotating or moving the whole treatment head, only the collimation of the radiation field follows the translation of the patient. In this way, the radiation field center can be configured to follow the movement of the isocenter defined in the patient during treatment planning. The advantages of this system include simpler design/structure and cost reduction. The gantry is mechanically stable and can achieve very high precision in delivery. Moreover, CT imaging can easily be integrated on the system for image guidance. The treatment couch only needs three translational motion freedoms.

Figure 2:
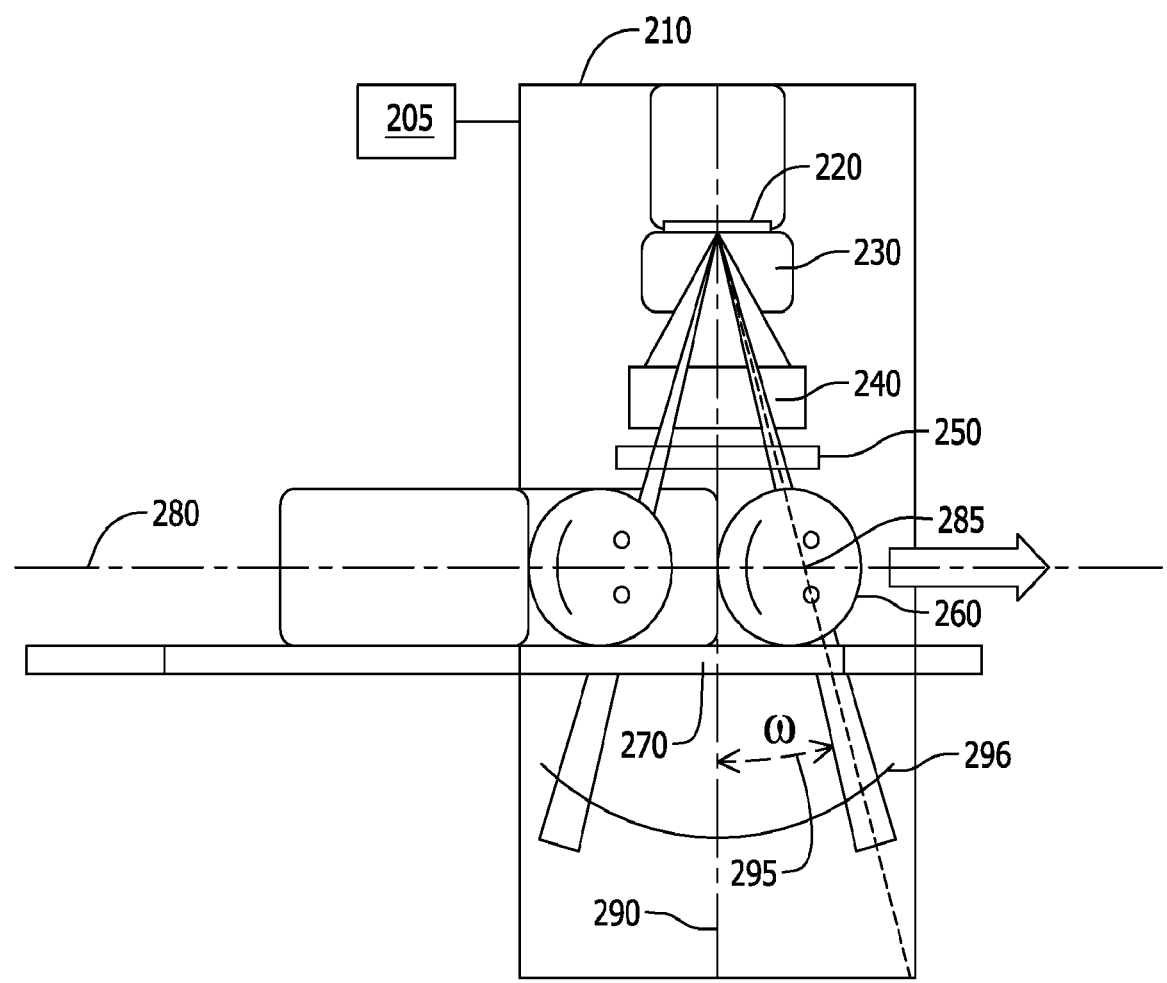
FIG. 2 shows an exemplary embodiment of the system for optimizing non-coplanar delivery without a gimbal head.

FIG. 2 shows an exemplary embodiment of the system for optimizing non-coplanar delivery without a gimbal head. The exemplary embodiment comprises a control unit 205, a gantry 210, a radiation treatment source 220, a first collimator 230, a second collimator 240, a third collimator 250, a patient 260, and a couch 270. The gantry 210 is preferably a rotatable ring gantry; however, the gantry 210 can comprise other types of a gantry such as a C-arm gantry. The gantry 210 is configured to rotate around a body of the patient 260 positioned along with a longitudinal axis 280. The radiation treatment source 220 is preferably a LINAC; however, the radiation treatment source 220 can comprise other types of radiation sources such as co-60. The radiation treatment source 220 is configured to emit the x-ray treatment beam in a direction that is traverse to the longitudinal axis 280. An additional portal imager 296 can be installed for treatment beam and patient setup verification. In one embodiment, the x-ray treatment beam is emitted in a direction that is substantially perpendicular to the longitudinal axis 280.

The first collimator 230 is configured to block peripheral radiation emitted from the radiation treatment source 220. Preferably, the first collimator 230 collimates the x-ray treatment beam to its maximum field size. The second collimator 240 is configured to collimate the x-ray treatment beam collimated by the first collimator 230. The radiation field collimated by the first collimator 230 is larger than the radiation field collimated by the second collimator 240. Preferably, the second collimator 240 can be configured to collimate the x-ray treatment beam to a rectangular shape field that is large enough to enclose the whole target in the patient's body. Alternatively, the second collimator 240 can be configured to collimate the x-ray treatment beam to a field that encompasses at least a partial target volume. The third collimator 250 is configured to collimate the x-ray treatment beam emitted from the second collimator 240. Preferably, the third collimator 250 is configured to collimate the x-ray treatment beam to the actual shape of the radiation field. The radiation field collimated by the second collimator 240 is larger than the field collimated by the third collimator 250.

In operation, the radiation treatment source 220 and the first collimator 230 are affixed to the gantry 210. The second collimator 240 and the third collimator 250 are movably attached to the gantry 210. The couch 270 is configured to translate along the longitudinal axis 280. When the couch 270 moves, the target of the patient also moves with the couch 270 along the longitudinal axis 280. During such movement, the second collimator 240 and third collimator 250 also move along the longitudinal axis 280. The second collimator 240 is preferably configured to move out of a gantry rotation plane 290 along said longitudinal axis 280 such that the second collimator 240 collimates the beam to the third collimator 250. The third collimator 250 is preferably configured to move along with the second collimator 240 such that the beam collimated by the third collimator 250 follows the isocenter 285 while the patient 260 moves along the longitudinal axis 280. The movement of the second collimator 240 and/or third collimator 250 can be in a form of rotational movement, tilting movement, or translation movement. In case of the rotational movement, the second collimator 240 and/or third collimator 250 rotate about a source point of the radiation treatment source 220. In case of tilting movement, the second collimator 240 and/or third collimator 250 tilt on the gantry rotation plane. In case of the translational movement, second collimator 240 and/or the third collimator translate along the longitudinal axis 280. In any movement, the field center always tracks the isocenter 285 in the patient.

Figure 7:
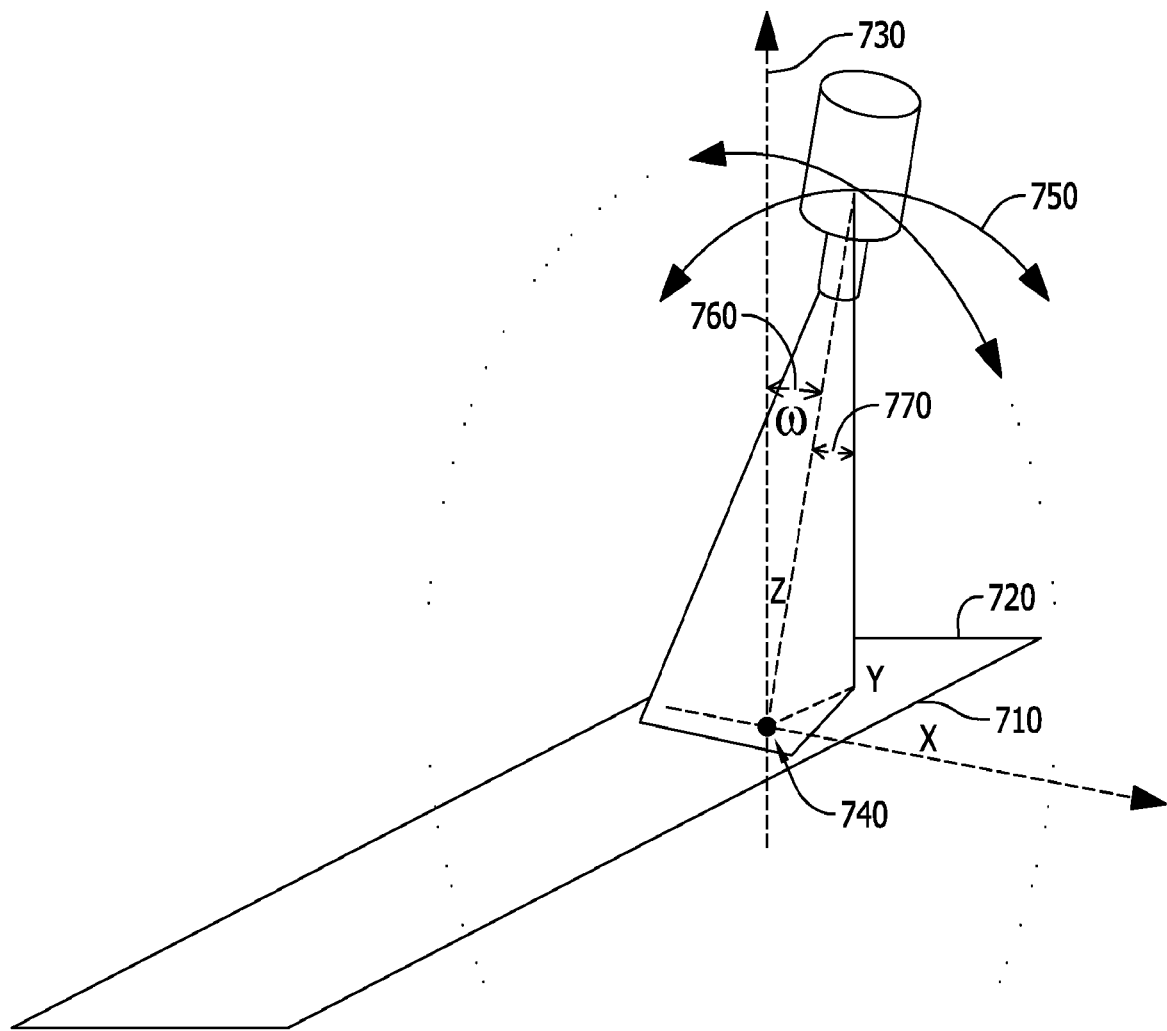
FIG. 7 shows an exemplary embodiment for the coordinate system of the system for optimizing non-coplanar delivery without a gimbal head.

The control unit 205 can be configured to control the movement of the second collimator 240 and/or third collimator 250. Preferably, the control unit 205 controls the movement of the second collimator 240 and/or the third collimator 250 by a plurality of non-coplanar angles ω 295 relative to the gantry rotation plane 290. The non-coplanar angle ω 295 represents an angle of the center of the x-ray treatment beam aligned with the isocenter of the treatment beams in relative to the gantry rotation plane 290 as shown in FIGS. 2 and 7.

The control unit 205 can reside on the gantry 210 or be a part of the gantry 210. The control unit 205 also can be a separate device, component, or computer that is remotely connected to the gantry 210.

In another embodiment, the control unit 205 can be configured to control not only the third collimator 250 but also other components such as the x-ray radiation source 220, the second collimator 240, and/or the couch 270. In this embodiment, a user or operator can use the control unit 205 to initiate the treatment or adjust the movements of the collimators, x-ray radiation source 220, and couch 270.

In another embodiment, only the first collimator 230 and the second collimator 240 can be used to collimate the x-ray treatment beam. In this embodiment, the third collimator 250 is not used. Instead, the second collimator 240 is configured to collimate the x-ray treatment beam such that the beam follows the isocenter in the patient's body during treatment.

During treatment delivery, the couch translation can be continuous or step-and-shoot. If continuous, the source trajectory is helical in patient's point of view. If step-and-shoot, the source trajectory is multiple circles at different longitudinal positions. As shown in FIG. 2, when the isocenter is out of the gantry rotation plane 290, the treatment beam forms the non-coplanar angle ω 295 with respect to the gantry rotation plane 290. The treatment beam forms a cone when the source rotates. By rotating or moving the second collimator 240 and/or the third collimator 250, the treatment beam forms a non-coplanar cone shaped beam in a helical mode.

Figure 3:
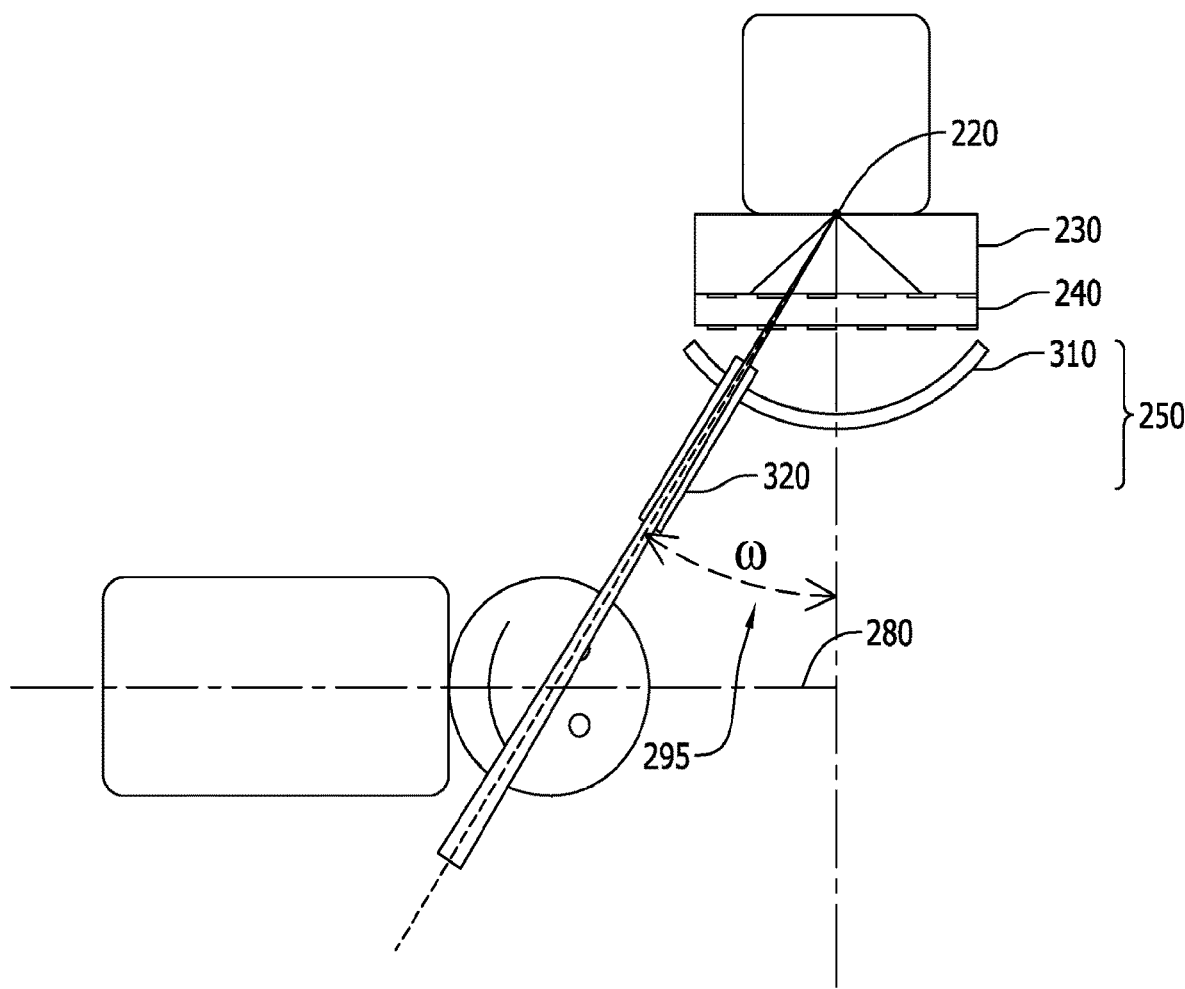
FIG. 3 shows a first exemplary embodiment of the third collimator shown in FIG. 2.

FIG. 3 shows a first exemplary embodiment of the third collimator 250. In this embodiment, the third collimator 250 comprises a guiding rail 310 and a cone collimator 320. The guiding rail 310 is affixed to the gantry 210, shown in FIG. 2. The cone collimator 320 is movably attached to the guiding rail 310. The cone collimator 320 is configured to collimate the x-ray treatment beam collimated by the second collimator 240 in a direction of the isocenter point in the patient's body. Preferably, the cone collimator 320 is configured to move along the guiding rail 310 relative to the movement of the patient. By moving along the guiding rail 310, the beam collimated by the cone collimator 320 can be adjusted to follow the target while the patient moves along the longitudinal axis 280. In this embodiment, the cone collimator 320 is preferably used to treat relatively small targets. For example, the cone collimator 320 can be configured to collimate the beam to a pencil beam. The beam diameter can be determined by the cone collimator insert 322. Preferably, the beam diameter of the cone collimator 320 can be configured to range from 2 mm to 20 mm. However, it should be understood that this is provided only as an example and should not be used to limit the scope of the present invention.

Figure 4A:
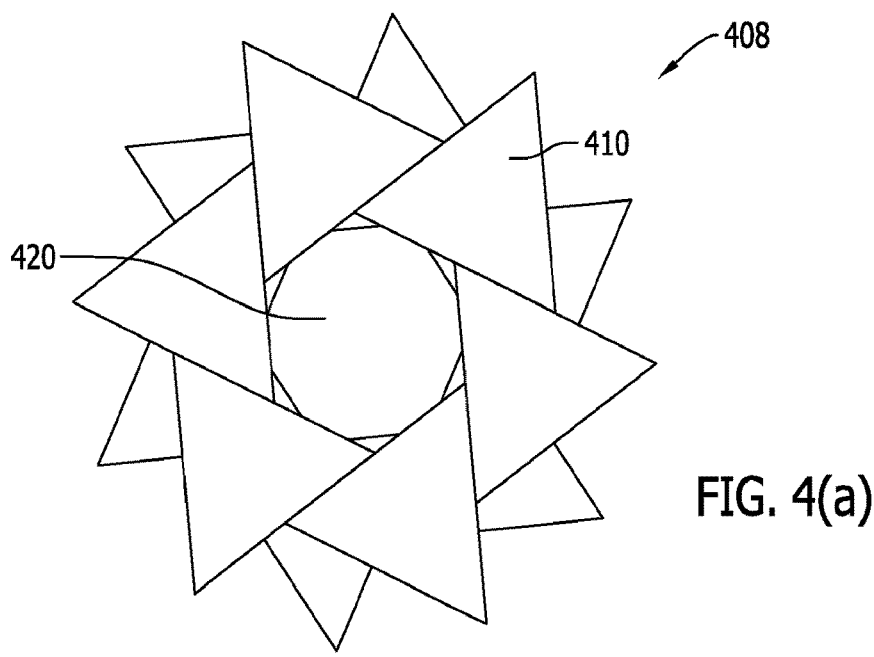
FIG. 4(a) shows an exemplary embodiment of an iris aperture.
Figure 4B:
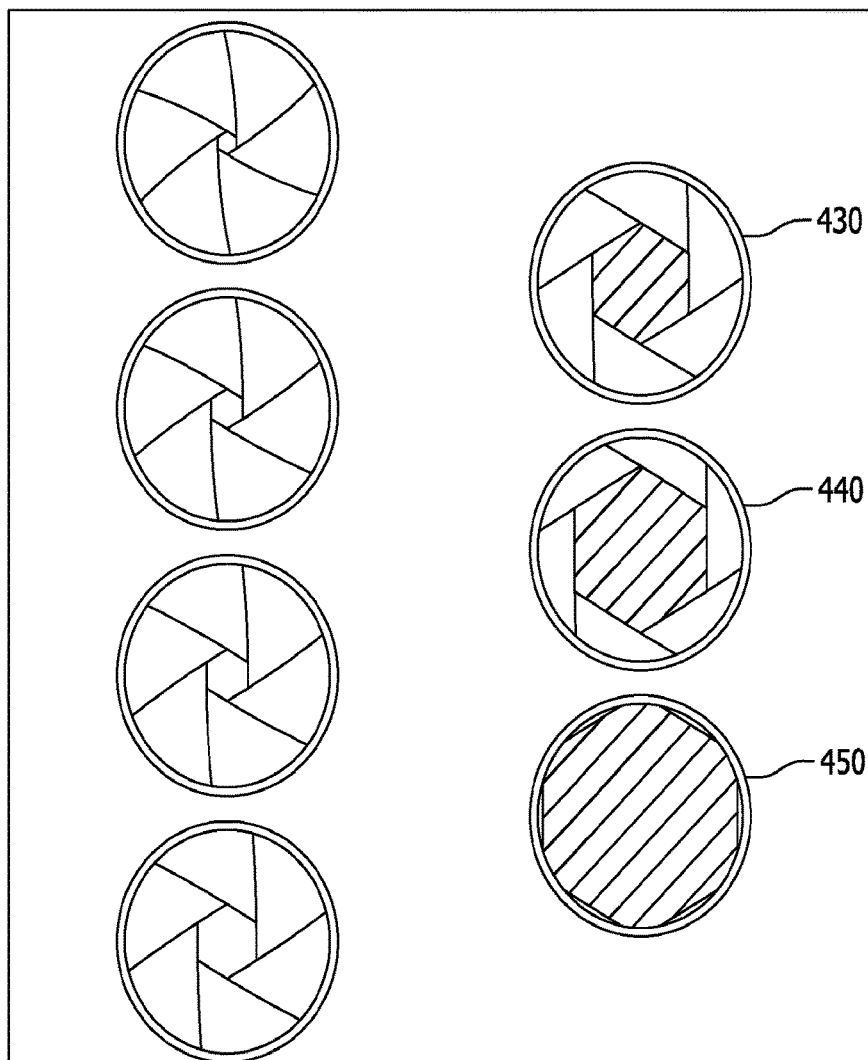
FIG. 4(b) shows an exemplary embodiment of a multi-layer iris aperture.

In one embodiment, the cone collimator 320 comprises an iris aperture 408 as shown in FIG. 4(*a*). In this embodiment, the iris aperture 408 replaces the cone collimator 320 and includes a plurality of layers 410, which can be configured to move in order to change an aperture size 420 of the iris aperture at different layer levels. For example, as shown in FIG. 4(*b*), the layers can be configured to move in order to gradually change the size of the aperture size at different levels, 430 being a smaller aperture size and 450 being a larger aperture size with 440 being an aperture size between 430 and 450. Only two layers are shown in this example; however, any number of layers can be implemented in order to accomplish this goal. In one embodiment, the control unit 205 can be configured to control the movement of the layers 410.

Figure 5:
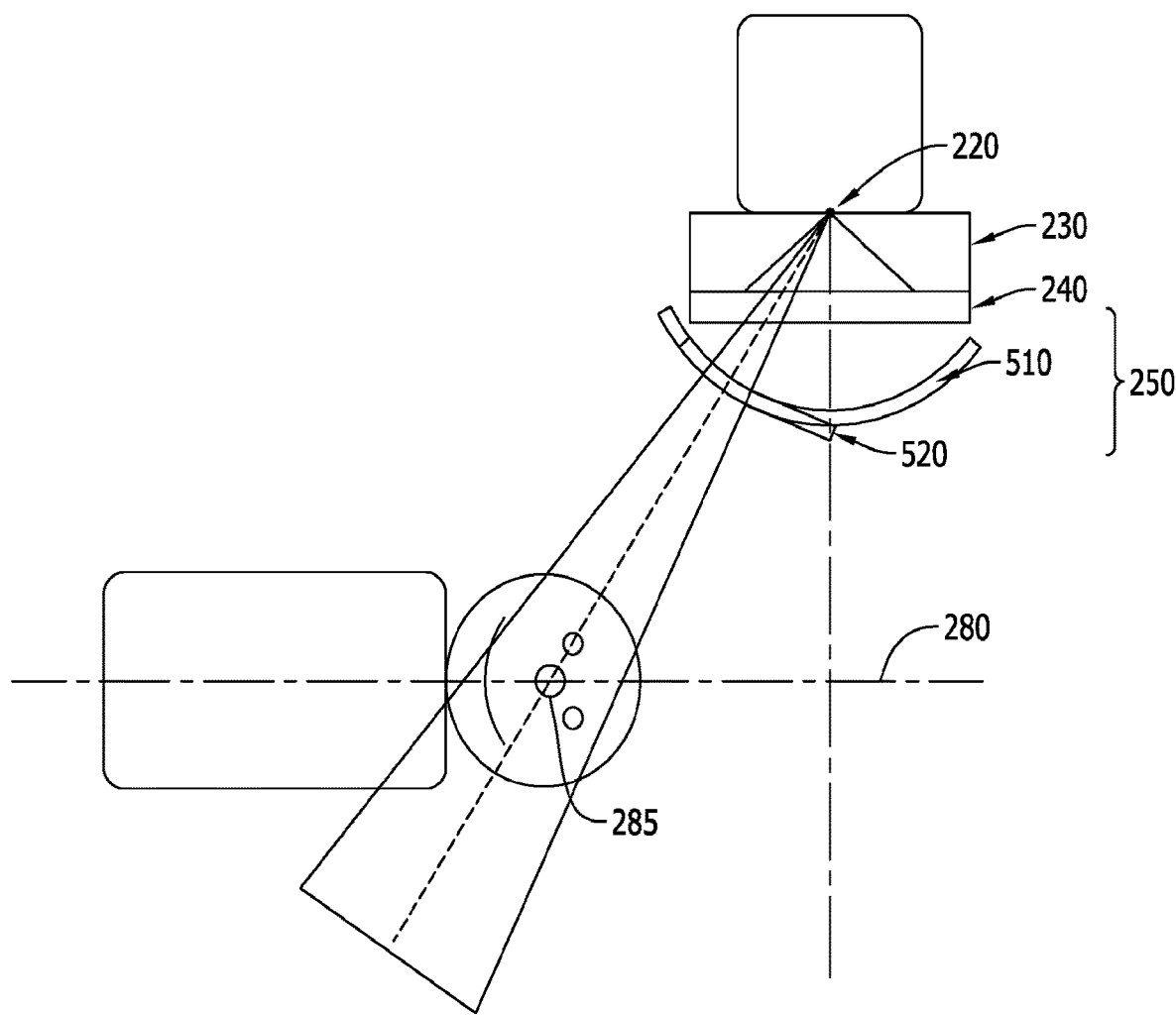
FIG. 5 shows a second exemplary embodiment of the third collimator shown in FIG. 2.

FIG. 5 shows a second exemplary embodiment of the third collimator 250. In this embodiment, the third collimator 250 comprises a rotatable cartridge 510 and a multi-leaf collimator 520. The rotatable cartridge 510 is preferably mounted on a structure like the guiding rail 310 of FIG. 3 that is affixed to the gantry 210, shown in FIG. 2. The multi-leaf collimator 520 is affixed to the rotatable cartridge 510. The multi-leaf collimator 520 is configured to collimate the x-ray treatment beam collimated by the second collimator 240 in a direction of the target in the patient's body. Preferably, the rotatable cartridge 510 is configured to move relative to the movement of the patient. By having the rotatable cartridge 510 that moves along the patient, the beam collimated by the multi-leaf collimator 520 can be adjusted to follow the target while the patient 260 moves along the longitudinal axis 280. In this embodiment, the multi-leaf collimator 520 is preferably a single-layer multi-leaf collimator. The multi-leaf collimator 520 is preferably used to treat targets that are relatively larger than the targets that can be used for the cone collimator 320 of FIG. 3. For example, the multi-leaf collimator can be configured to collimate the beam to a field size of 20 cm×40 cm. However, this should be understood that this is provided only as an example and should not be used to limit the scope of the present invention.

Figure 6:
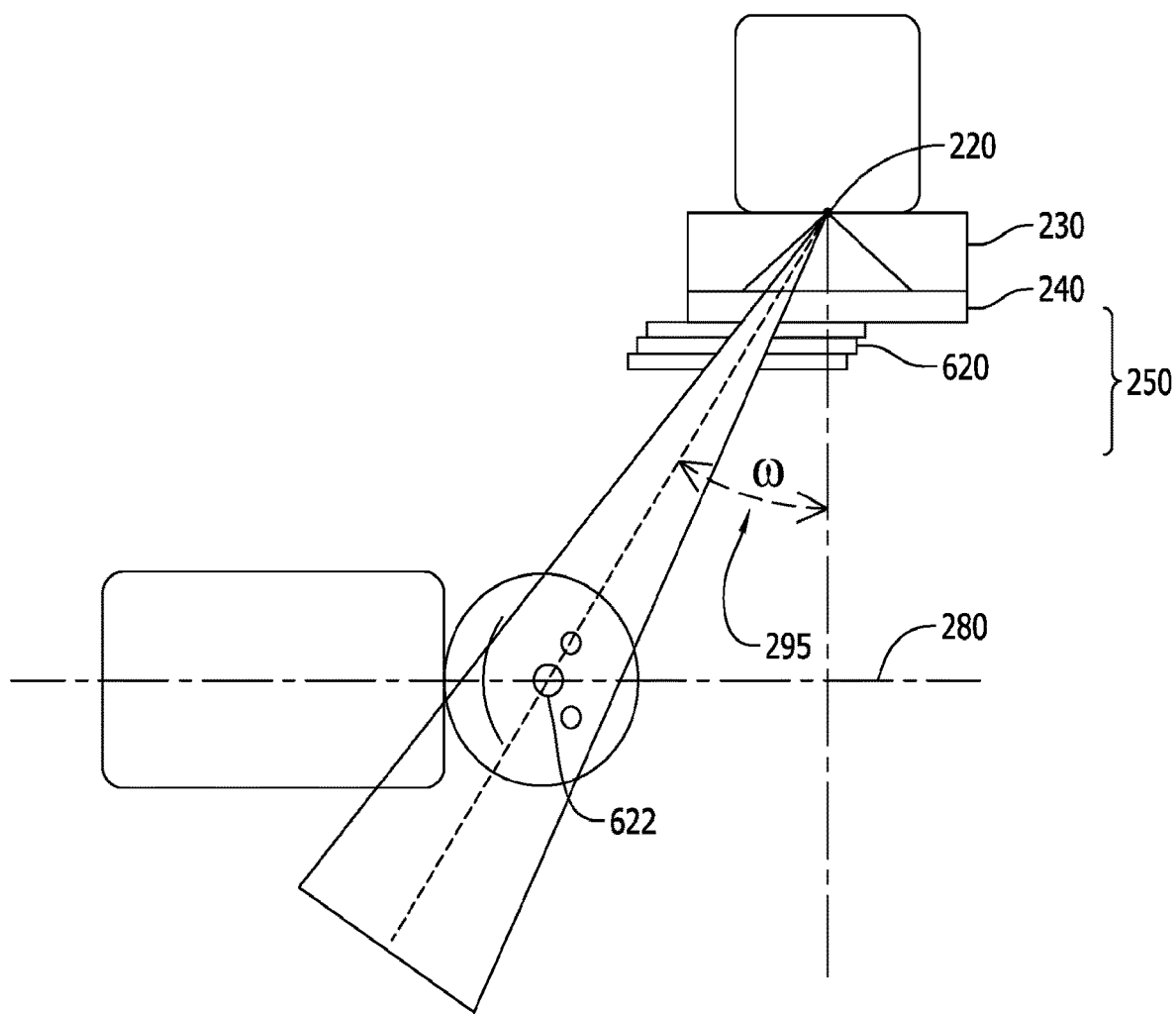
FIG. 6 shows a third exemplary embodiment of the third collimator shown in FIG. 2.

FIG. 6 shows a third exemplary embodiment of the third collimator 250. In this embodiment, the third collimator 250 comprises a non-rotating cartridge (not shown) and a multi-leaf collimator 620. The non-rotatable cartridge is affixed to the gantry 210, as shown in FIG. 2. The multi-leaf collimator 620 is affixed to the non-rotatable cartridge. The multi-leaf collimator 620 is configured to collimate the x-ray treatment beam collimated by the second collimator 240 in a direction of the target in the patient's body. Preferably, the multi-leaf collimator 620 comprises a plurality of layers such that one or more layers can be configured to collimate the beam to follow the movement of the patient 260. The beam collimated by the multi-leaf collimator 620 can be adjusted to follow the target or isocenter 622 while the patient 260 moves along the longitudinal axis 280. In this embodiment, the tips of leaves at different layers may be positioned to follow a divergence angle of the radiation treatment beam so that the radiation beam can have a sharper penumbra at larger non-coplanar angle.

In another embodiment, the non-rotating cartridge can be configured to translate out of the gantry rotation plane along the longitudinal axis 280. The translation movement of the non-rotating cartridge can further expand the range of distance that the beam can travel along the longitudinal axis 280, providing more distance to the range that the leaves of the multi-leaf collimator 620 can translate. Preferably, the control unit 205 is configured to control the movement of the third collimator 250 by rotating the third collimator 250 by a plurality of non-coplanar angles relative to the gantry rotation plane.

FIG. 7 shows an exemplary embodiment for the coordinate system of the system for optimizing non-coplanar delivery without a gimbal head. In this exemplary embodiment, the coordinate system and the beam parameters are defined using International Electrotechnical Commission (IEC) coordinate system convention set forth in Medical Electron Accelerators—Functional Performance Characteristics, IEC Performance Standard 976, October 1989. For a patient laying supine on the treatment couch with his/her head towards the gantry, an x-axis 710 runs from patient's right to left, a y-axis 720 runs from inferior to superior direction and a z-axis 730 runs from posterior to anterior direction. The origins of the x, y and z axes are located at an isocenter 740. The longitudinal axis 280 of FIG. 2 is the axis where x=0 and z=0. In the exemplary coordinate system, the gantry 210 of FIG. 2 rotates along a gantry rotation plane 750. The second collimator 240 and/or the third collimator 250 of FIG. 2 are configured to move out of the gantry rotation plane 750 along the longitudinal axis 280, creating a non-coplanar angle ω 760. The movement of the gantry 210 creates a gantry angle 770.

During radiosurgery, a patient needs to be positioned exactly the same orientation as the simulation CT scans. A full rigid body correction has three translational and three rotational components. Mostly, a treatment couch can only perform translational correction with one degree of rotation correction at most. Rotation angles are often neglected during regular treatments. In order to perform full six degree correction, some LINAC vendors provide special treatment couches that can translate and rotate. Without robotic or hexpod couch, rotation correction can be performed by rotating a couch, gantry and collimator altogether such as one disclosed in *A Method to Implement Full Six-Degree Target Shift Corrections for Rigid Body in Image-guided Radiotherapy*, Ning J. Yue, Jonathan P. S. Knisely, Hajun Song, and Ravinder Nath, Medical Physics 33, 21-31 (2006). Nevertheless, this method is inconvenient to use, and the patient has to rotate in large angles even for a very small pitch correction.

Another advantage of the system for optimizing non-coplanar delivery without a gimbal head is to perform rotation setup correction by rotating the treatment beam of a patient instead of a treatment couch. The proposed system can be configured to correct a rotational setup error. With the movement of the second and/or third collimator, the patient does not need to rotate. After translated to the isocenter, the rotation components can be corrected by gantry, gimbal and collimator rotations. This eliminates the complex robotic couch. This method is also applicable to the conventional gimbal rotation approaches described in U.S. Pat. No. 6,969,194 or a CyberKnife® machine.

In the system for optimizing non-coplanar delivery without a gimbal head, the beam vector B of an x-ray treatment beam can be defined with a gantry angle θ, non-coplanar angle ω and collimator angle α. Preferably, the collimator angle α is an angle by which the third collimator 250 of FIG. 2 rotates about its central axis. In cases where the third collimator 250 is a cone collimator, the collimator angle α is irrelevant since the radiation beam is rotational invariable. In cases where the third collimator 250 is a multi-leaf collimator, the collimator angle α is a rotation angle of the leaves of the third collimator 250.

For the machines with gimbal rotation capacities, including CyberKnife, and those shown in FIG. 5-7, non-coplanar beams delivery are achieved directly by gimbal rotation. The vector for a beam with gantry angle θ and gimbal angle ω is calculated by $$B = R_y^\theta \otimes R_x^\omega \otimes k = \begin{pmatrix} \cos\theta & 0 & \sin\theta \\ 0 & 1 & 0 \\ -\sin\theta & 0 & \cos\theta \end{pmatrix} \begin{pmatrix} 1 & 0 & 0 \\ 0 & \cos\omega & -\sin\omega \\ 0 & \sin\omega & \cos\omega \end{pmatrix} \begin{pmatrix} 0 \\ 0 \\ 1 \end{pmatrix} = \begin{pmatrix} \sin\theta\cos\omega \\ -\sin\omega \\ \cos\theta\cos\omega \end{pmatrix}$$

where $R_x^\omega$, is x rotation matrix.

During an IGRT treatment, 3D image registration between online and reference images determines a setup error with three translational components ($\Delta x$, $\Delta y$ and $\Delta z$) and three rotational components ($\sigma_x$, $\sigma_y$ and $\sigma_z$). Translational setup error is corrected by shifting the treatment couch, which is straightforward and ignored in the derivation below. To correct rotational setup error, instead of rotating the patient $\sigma_x \to \sigma_y \to \sigma_z$ sequentially, one can rotate the treatment beam B in the order $-\sigma_z \to -\sigma_y \to -\sigma_x$. This sequential rotation operation will keep the beam the same orientation with respect to the patient. In the patient's coordinate, the new beam vector B' is obtained by, $$B' = R_x^{-\sigma_x} \otimes R_y^{-\sigma_y} \otimes R_z^{-\sigma_z} \otimes B =$$

$$\begin{pmatrix} 1 & 0 & 0 \\ 0 & \cos\sigma_x & \sin\sigma_x \\ 0 & -\sin\sigma_x & \cos\sigma_x \end{pmatrix} \begin{pmatrix} \cos\sigma_y & 0 & -\sin\sigma_y \\ 0 & 1 & 0 \\ \sin\sigma_y & 0 & \cos\sigma_y \end{pmatrix} \begin{pmatrix} \cos\sigma_z & \sin\sigma_z & 0 \\ -\sin\sigma_z & \cos\sigma_z & 0 \\ 0 & 0 & 1 \end{pmatrix}$$

$$\begin{pmatrix} \sin\theta\cos\omega \\ -\sin\omega \\ \cos\theta\cos\omega \end{pmatrix} = \begin{pmatrix} 1 & 0 & 0 \\ 0 & \cos\sigma_x & \sin\sigma_x \\ 0 & -\sin\sigma_x & \cos\sigma_x \end{pmatrix} \begin{pmatrix} \cos\sigma_y & 0 & -\sin\sigma_y \\ 0 & 1 & 0 \\ \sin\sigma_y & 0 & \cos\sigma_y \end{pmatrix}$$

$$\begin{pmatrix} \sin\theta\cos\omega\cos\sigma_z - \sin\omega\sin\sigma_z \\ -\sin\omega\cos\omega\sin\sigma_z - \sin\omega\cos\sigma_z \\ \cos\theta\cos\omega \end{pmatrix} = \begin{pmatrix} 1 & 0 & 0 \\ 0 & \cos\sigma_x & \sin\sigma_x \\ 0 & -\sin\sigma_x & \cos\sigma_x \end{pmatrix}$$

$$\begin{pmatrix} \sin\theta\cos\omega\cos\sigma_y\cos\sigma_z - \sin\omega\cos\sigma_y\sin\sigma_z - \\ \cos\theta\cos\omega\sin\sigma_y \\ -\sin\theta\cos\omega\sin\sigma_z - \sin\omega\cos\sigma_z \\ \sin\theta\cos\omega\sin\sigma_y\cos\sigma_z - \sin\omega\sin\sigma_y\sin\sigma_z + \\ \cos\theta\cos\omega\cos\sigma_y \end{pmatrix} =$$

$$\begin{pmatrix} \sin\theta\cos\omega\cos\sigma_y\cos\sigma_z - \sin\omega\cos\sigma_y\sin\sigma_z - \\ \cos\theta\cos\omega\sin\sigma_y \\ -\sin\theta\cos\omega\cos\sigma_x\sin\sigma_z - \sin\omega\cos\sigma_x\cos\sigma_z + \\ \sin\theta\cos\omega\sin\sigma_x\sin\sigma_y\cos\sigma_z - \sin\omega\sin\sigma_x\sin\sigma_y\sin\sigma_z + \\ \cos\theta\cos\omega\sin\sigma_x\cos\sigma_y \\ \sin\theta\cos\omega\sin\sigma_x\sin\sigma_x + \sin\omega\sin\sigma_x\cos\sigma_z + \\ \sin\theta\cos\omega\cos\sigma_x\sin\sigma_y\cos\sigma_z - \sin\omega\cos\sigma_x\sin\sigma_y\sin\sigma_z + \\ \cos\theta\cos\omega\cos\sigma_x\cos\sigma_y \end{pmatrix}$$

The new gantry angle θ' is obtained by, $$\theta' = \tan^{-1}\left(\frac{B'_x}{B'_z}\right) =$$

$$\tan^{-1}\left(\frac{\sin\theta\cos\omega\cos\sigma_y\cos\sigma_z - \sin\omega\cos\sigma_y\sin\sigma_z - \cos\theta\cos\omega\sin\sigma_y}{\sin\theta\cos\omega\sin\sigma_x\sin\sigma_z + \sin\omega\sin\sigma_x\cos\sigma_z + \sin\theta\cos\omega\cos\sigma_x\sin\sigma_y\cos\sigma_z - \sin\omega\cos\sigma_x\sin\sigma_y\sin\sigma_z + \cos\theta\cos\omega\cos\sigma_x\cos\sigma_y}\right)$$

The new gimbal angle ω' is obtained by, $$\omega' = -\sin^{-1}(B'_y) = -\sin^{-1}(-\sin\theta\cos\omega\cos\sigma_x\sin\sigma_z - \sin\omega\cos\sigma_x\cos\sigma_z + \sin\theta\cos\omega\sin\sigma_x\sin\sigma_y\cos\sigma_z - \sin\omega\sin\sigma_x\sin\sigma_y\sin\sigma_z + \cos\theta\cos\omega\sin\sigma_x\cos\sigma_y)$$

The radiation treatment fields are defined by cone or MLC. While cone collimator is rotational invariant, the fields defined by MLC have a rotation angle should also be adjusted to reproduce the same orientation relative to the patient. We define a collimator vector C coinciding with vector j when gantry, gimbal and collimator angles are all zero. For a radiation field with gantry angle θ, gimbal angle ω and collimator angle α, the collimator vector becomes $$C = R_y^\theta \otimes R_x^\omega \otimes R_z^\alpha \otimes j =$$

$$\begin{pmatrix} \cos\theta & 0 & \sin\theta \\ 0 & 1 & 0 \\ -\sin\theta & 0 & \cos\theta \end{pmatrix} \begin{pmatrix} 1 & 0 & 0 \\ 0 & \cos\omega & -\sin\omega \\ 0 & \sin\omega & \cos\omega \end{pmatrix} \begin{pmatrix} \cos\alpha & -\sin\alpha & 0 \\ \sin\alpha & \cos\alpha & 0 \\ 0 & 0 & 1 \end{pmatrix} \begin{pmatrix} 0 \\ 1 \\ 0 \end{pmatrix} =$$

$$\begin{pmatrix} -\cos\theta\sin\alpha + \sin\theta\sin\omega\cos\alpha \\ \cos\omega\cos\alpha \\ \sin\theta\sin\alpha + \cos\theta\sin\omega\cos\alpha \end{pmatrix}$$

Similarly to the beam vector, the collimator vector needs to rotate $-\sigma_z \rightarrow -\sigma_y \rightarrow -\sigma_x$ sequentially to correct the rotational setup error. Thereby the new collimator vector C' after rotation correction is $$C' = R_x^{-\sigma_x} \otimes R_y^{-\sigma_y} \otimes R_z^{-\sigma_z} \otimes C$$

$$\begin{pmatrix} 1 & 0 & 0 \\ 0 & \cos\sigma_x & \sin\sigma_x \\ 0 & -\sin\sigma_x & \cos\sigma_x \end{pmatrix} \begin{pmatrix} \cos\sigma_y & 0 & -\sin\sigma_y \\ 0 & 1 & 0 \\ \sin\sigma_y & 0 & \cos\sigma_y \end{pmatrix}$$

$$\begin{pmatrix} \cos\sigma_z & \sin\sigma_z & 0 \\ -\sin\sigma_x & \cos\sigma_x & 0 \\ 0 & 0 & 1 \end{pmatrix} \begin{pmatrix} -\cos\theta\cos\alpha + \sin\theta\sin\omega\sin\alpha \\ \cos\omega\sin\alpha \\ \sin\theta\cos\alpha + \cos\theta\sin\omega\sin\alpha \end{pmatrix}$$

$$\begin{pmatrix} -\cos\theta\cos\alpha\cos\sigma_y\cos\sigma_z + \sin\theta\sin\omega\sin\alpha\cos\sigma_y\cos\theta_z + \\ \cos\omega\sin\alpha\cos\alpha_y\sin\sigma_z - \sin\theta\cos\alpha\sin\sigma_y - \cos\theta\sin\omega\sin\alpha\sin\sigma_y \\ \cos\theta\cos\alpha\cos\sigma_z\sin\sigma_z - \sin\theta\sin\omega\sin\alpha\cos\sigma_z\sin\sigma_z + \\ \cos\omega\sin\alpha\cos\sigma_z\cos\sigma_z - \cos\theta\cos\alpha\sin\sigma_z\sin\sigma_y\cos\sigma_z + \\ \sin\theta\sin\omega\sin\alpha\sin\sigma_z\sin\sigma_y\cos\sigma_z + \cos\omega\sin\alpha\sin\sigma_z\sin\sigma_y\sin\sigma_z + \\ \sin\theta\cos\alpha\sin\sigma_z\cos\sigma_y - \cos\theta\sin\omega\sin\alpha\sin\sigma_x\cos\sigma_y \\ -\cos\theta\cos\alpha\sin\sigma_z\sin\sigma_z + \sin\theta\sin\omega\sin\alpha\sin\sigma_z\sin\sigma_z - \\ \cos\omega\sin\alpha\sin\sigma_x\cos\sigma_z - \cos\theta\cos\alpha\cos\sigma_z\sin\sigma_y\cos\sigma_z + \\ \sin\theta\sin\omega\sin\alpha\cos\sigma_x\sin\sigma_y\cos\sigma_z + \cos\omega\sin\alpha\cos\sigma_z\sin\sigma_y\sin\sigma_z + \\ \sin\theta\cos\alpha\cos\sigma_z\cos\sigma_y + \\ \cos\theta\sin\omega\sin\alpha\cos\sigma_x\cos\sigma_y \end{pmatrix}$$

The collimator angle is the angle between gimbal rotation plane and collimator vector. Gimbal rotation plane is represented by a vector G that is perpendicular to the gimbal rotation plane, $$G = R_y^\theta \otimes i = \begin{pmatrix} \cos\theta & 0 & \sin\theta \\ 0 & 1 & 0 \\ -\sin\theta & 0 & \cos\theta \end{pmatrix} \begin{pmatrix} 1 \\ 0 \\ 0 \end{pmatrix} = \begin{pmatrix} \cos\theta \\ 0 \\ -\sin\theta \end{pmatrix}$$

The new collimator angle is obtained by $$\alpha' = \cos^{-1}(G \cdot C') = \cos^{-1}$$

$$\begin{pmatrix} \begin{pmatrix} \cos\theta \\ 0 \\ -\sin\theta \end{pmatrix} \cdot \begin{pmatrix} -\cos\theta\cos\alpha\cos\sigma_y\cos\sigma_z + \\ \sin\theta\sin\omega\sin\alpha\cos\sigma_x\cos\sigma_z + \\ \cos\omega\sin\alpha\cos\sigma_y\sin\alpha_z - \\ \sin\theta\cos\alpha\sin\sigma_y - \cos\theta\sin\omega\sin\alpha\sin\sigma_y \\ \cos\theta\cos\alpha\cos\sigma_z\sin\sigma_z - \sin\theta\sin\omega\sin\alpha\cos\sigma_x\sin\sigma_z + \\ \cos\omega\sin\alpha\cos\sigma_z\cos\sigma_z - \\ \cos\theta\cos\alpha\sin\sigma_z\sin\sigma_y\cos\sigma_z + \\ \sin\theta\sin\omega\sin\alpha\sin\sigma_z\sin\sigma_y\cos\sigma_z + \\ \cos\omega\sin\alpha\sin\sigma_x\sin\sigma_y\sin\sigma_z + \\ \sin\theta\cos\alpha\sin\sigma_z\cos\sigma_y + \\ \cos\theta\sin\omega\sin\alpha\sin\sigma_z\cos\sigma_y \\ -\cos\theta\cos\alpha\sin\sigma_x\sin\sigma_z + \sin\theta\sin\omega\sin\alpha\sin\sigma_x\sin\sigma_z - \\ \cos\omega\sin\alpha\sin\sigma_x\cos\sigma_z - \cos\theta\cos\alpha\cos\sigma_x\sin\sigma_y\cos\sigma_z + \\ \sin\theta\sin\omega\sin\alpha\cos\sigma_x\sin\sigma_y\cos\sigma_z + \\ \cos\omega\sin\alpha\cos\sigma_x\sin\sigma_y\sin\sigma_z + \\ \sin\theta\cos\alpha\cos\sigma_z\cos\sigma_y - \cos\theta\sin\omega\sin\alpha\cos\sigma_x\cos\sigma_y \end{pmatrix} \end{pmatrix} =$$

$$\cos^{-1}(-\cos^2\theta\cos\alpha\cos\sigma_y\cos\sigma_z - \sin\theta\cos\theta\sin\omega\sin\alpha\cos\sigma_y\cos\sigma_z +$$
$$\cos\theta\cos\omega\sin\alpha\cos\sigma_y\sin\sigma_2 - \sin\theta\cos\theta\cos\alpha\sin\sigma_y -$$
$$\cos^2\theta\sin\omega\sin\alpha\sin\sigma_{y-} + \sin\theta\cos\theta\cos\alpha\sin\sigma_x\sin\sigma_z -$$
$$\sin^2\theta\sin\omega\sin\alpha\sin\sigma_x\sin\sigma_z + \sin\theta\cos\omega\sin\alpha\sin\sigma_x\cos\sigma_z +$$
$$\sin\theta\cos\theta\cos\alpha\cos\sigma_x\sin\sigma_y\cos\sigma_z - \sin^2\theta\sin\omega\sin\alpha\cos$$
$$\sigma_x\sin\sigma_y\cos\sigma_z - \sin\theta\cos\omega\sin\alpha\cos\sigma_x\sin\sigma_y\sin\sigma_z -$$
$$\sin^2\theta\cos\alpha\cos\sigma_x\cos\sigma_y - \sin\theta\cos\theta\sin\omega\sin\alpha\cos\sigma_x\cos\sigma_y)$$

Assuming through an image guidance procedure, 3D image registration determines a shift of Δx, Δy and Δz and a rotation correction of $\sigma_x$, $\sigma_y$ and $\sigma_z$ are needed to set-up the patient properly. The shift is performed by translating the treatment couch, which is straightforward. For rotation correction, instead of rotating the patient, the beam can be rotated $-\sigma_x$, $-\sigma_y$ and $-\sigma_z$, so that orientation remains the same with respect to the patient. Thus the new beam vector is obtained by, $$B' = R_z^{-\sigma_z} \otimes R_y^{-\sigma_y} \otimes R_x^{-\sigma_x} \otimes B =$$

$$\begin{pmatrix} \cos\sigma_z & -\sin\sigma_z & 0 \\ \sin\sigma_z & \cos\sigma_z & 0 \\ 0 & 0 & 1 \end{pmatrix} \begin{pmatrix} \cos\sigma_y & 0 & -\sin\sigma_y \\ 0 & 1 & 0 \\ \sin\sigma_y & 0 & \cos\sigma_y \end{pmatrix} \begin{pmatrix} 1 & 0 & 0 \\ 0 & \cos\sigma_x & \sin\sigma_x \\ 0 & -\sin\sigma_x & \cos\sigma_x \end{pmatrix}$$

$$\begin{pmatrix} \sin\theta\cos\omega \\ -\sin\omega \\ \cos\theta\cos\omega \end{pmatrix} = \begin{pmatrix} \cos_z & -\sin\sigma_z & 0 \\ \sin\sigma_z & \cos\sigma_z & 0 \\ 0 & 0 & 1 \end{pmatrix} \begin{pmatrix} \cos\sigma_y & 0 & -\sin\sigma_y \\ 0 & 1 & 0 \\ \sin\sigma_y & 0 & \cos\sigma_y \end{pmatrix}$$

$$\begin{pmatrix} \sin\theta\cos\omega \\ -\cos\sigma_z\sin\omega + \sin\sigma_z\cos\theta\cos\omega \\ \sin\sigma_z\sin\omega + \cos\sigma_x\cos\theta\cos\omega \end{pmatrix} = \begin{pmatrix} \cos\sigma_z & -\sin\sigma_z & 0 \\ \sin\sigma_x & \cos\sigma_z & 0 \\ 0 & 0 & 1 \end{pmatrix}$$

$$\begin{pmatrix} \cos\sigma_y\sin\theta\cos\omega - \sin\sigma_y\sin\sigma_x\sin\omega - \sin\sigma_y\cos\sigma_x\cos\theta\cos\omega \\ -\cos\sigma_x\sin\omega + \sin\sigma_x\cos\theta\cos\omega \\ \sin\sigma_y\sin\theta\cos\omega + \cos\sigma_y\sin\sigma_x\sin\omega + \cos\sigma_y\cos\sigma_x\cos\theta\cos\omega \end{pmatrix} =$$

$$\begin{pmatrix} \cos\sigma_z\cos\sigma_y\sin\theta\cos\omega - \cos\sigma_x\sin\sigma_y\sin\sigma_z\sin\omega - \\ \cos\sigma_x\sin\sigma_y\cos\sigma_z\cos\theta\cos\omega + \sin\sigma_z\cos\sigma_x\sin\omega - \\ \sin\sigma_z\sin\sigma_x\cos\theta\cos\omega \\ \sin\sigma_x\cos\sigma_y\sin\theta\cos\omega - \sin\sigma_z\sin\sigma_y\sin\sigma_x\sin\omega - \\ \sin\sigma_x\sin\sigma_y\cos\sigma_z\cos\theta\cos\omega - \cos\sigma_z\cos\sigma_x\sin\omega + \\ \cos\sigma_x\sin\sigma_z\cos\theta\cos\omega \\ \sin\sigma_y\sin\theta\cos\omega + \cos\sigma_y\sin\sigma_x\sin\omega + \\ \cos\sigma_y\cos\sigma_x\cos\theta\cos\omega \end{pmatrix}$$

If rotation sequence is defined differently in image registration software, for example, rotate z→y→x, the final equation may be different. Similar equations can be derived in the same principle if rotation correction sequence is defined differently.

The new gantry angle θ' is obtained by, $$\theta' = \tan^{-1}\left(\frac{\cos\sigma_z\cos\sigma_y\sin\theta\cos\omega - \cos\sigma_x\sin\sigma_y\sin\sigma_z\sin\omega - \cos\sigma_x\sin\sigma_y\cos\sigma_z\cos\theta\cos\omega + \sin\sigma_z\cos\sigma_x\sin\omega - \sin\sigma_x\sin\sigma_z\cos\theta\cos\omega}{\sin\sigma_y\sin\theta\cos\omega + \cos\sigma_y\sin\sigma_x\sin\omega + \cos\sigma_y\cos\sigma_x\cos\theta\cos\omega}\right)$$

The new gimbal or non-coplanar angle ω' is obtained by,

ω'=sin⁻¹(sin σ_x cos σ_y sin θ cos ω−sin σ_x sin σ_y sin ω−sin σ_x sin σ_y cos σ_x cos θ cos ω−cos σ_x cos σ_x sin ω+cos σ_x sin σ_x cos θ cos ω)

Similarly, a new collimator angle for rotation correction can be derived. With initial collimator vector C with gimbal rotation, the new collimator vector C' after rotation correction is $C' =$ $$R_z^{-\sigma_z} \otimes R_y^{-\sigma_y} \otimes R_z^{-\sigma_z} \otimes C = \begin{pmatrix} \cos\sigma_z & \sin\sigma_z & 0 \\ -\sin\sigma_z & \cos\sigma_z & 0 \\ 0 & 0 & 1 \end{pmatrix}\begin{pmatrix} \cos\sigma_y & 0 & -\sin\sigma_y \\ 0 & 1 & 0 \\ \sin\sigma_y & 0 & \cos\sigma_y \end{pmatrix}$$

$$\begin{pmatrix} 1 & 0 & 0 \\ 0 & \cos\sigma_z & \sin\sigma_z \\ 0 & -\sin\sigma_z & \cos\sigma_z \end{pmatrix}\begin{pmatrix} \cos\theta\cos\alpha + \sin\theta\sin\omega\sin\alpha \\ \cos\omega\sin\alpha \\ -\sin\theta\cos\alpha + \cos\theta\sin\omega\sin\alpha \end{pmatrix} =$$

$$\begin{pmatrix} \cos\alpha_z & \sin\sigma_z & 0 \\ -\sin\alpha_z & \cos\alpha_z & 0 \\ 0 & 0 & 1 \end{pmatrix}\begin{pmatrix} \cos\sigma_y & 0 & -\sin\sigma_y \\ 0 & 1 & 0 \\ \sin\sigma_y & 0 & \cos\sigma_y \end{pmatrix}$$

$$\begin{pmatrix} \cos\theta\cos\alpha + \sin\theta\sin\omega\sin\alpha \\ \cos\sigma_z\cos\omega\sin\alpha - \sin\sigma_z\sin\theta\cos\alpha + \sin\sigma_z\cos\theta\sin\omega\sin\alpha \\ -\sin\sigma_z\cos\omega\sin\alpha + \cos\sigma_z\cos\theta\sin\omega\sin\alpha \end{pmatrix} = \begin{pmatrix} \cos\sigma_z & -\sin\sigma_z & 0 \\ \sin\sigma_z & \cos\sigma_z & 0 \\ 0 & 0 & 1 \end{pmatrix}$$

$$\begin{pmatrix} \cos\sigma_y\cos\theta\cos\alpha + \cos\sigma_y\sin\theta\sin\omega\sin\alpha + \\ \sin\sigma_y\sin\sigma_z\cos\omega\sin\alpha - \sin\sigma_y\cos\sigma_z\cos\theta\sin\omega\sin\alpha \\ \cos\sigma_z\cos\omega\sin\alpha - \sin\sigma_z\sin\theta\cos\alpha + \\ \sin\sigma_z\cos\theta\sin\omega\sin\alpha \\ \sin\sigma_y\cos\theta\cos\alpha + \sin\sigma_y\sin\theta\sin\omega\sin\alpha - \\ \cos\sigma_y\sin\sigma_z\cos\omega\sin\alpha + \\ \cos\sigma_y\cos\sigma_z\cos\theta\sin\omega\sin\alpha \end{pmatrix} =$$

$$\begin{pmatrix} \cos\sigma_z\cos\sigma_y\cos\theta\cos\alpha + \cos\sigma_z\cos\sigma_y\sin\theta\sin\omega\sin\alpha + \\ \cos\sigma_z\sin\sigma_y\sin\sigma_x\cos\omega\sin\alpha - \\ \sin\sigma_z\sin\sigma_y\cos\sigma_x\cos\omega\sin\alpha - \\ \sin\alpha_z\cos\sigma_x\cos\omega\sin\omega + \sin\alpha_z\sin\sigma_x\sin\sigma\sin\alpha - \\ \sin\sigma_z\sin\sigma_z\cos\theta\sin\omega\sin\sigma \\ \sin\sigma_z\cos\sigma_x\cos\theta\cos\alpha + \sin\sigma_z\cos\sigma_y\sin\theta\sin\omega\sin\alpha + \\ \sin\alpha_z\sin\alpha_y\sin\sigma_x\cos\omega\sin\omega - \\ \sin\alpha_z\sin\alpha_y\cos\theta_x\cos\theta\sin\omega\sin\alpha + \\ \cos\sigma_x\cos\sigma_z\cos\omega\sin\omega - \cos\sigma_x\sin\sigma_z\sin\theta\sin\alpha + \\ \cos\sigma_x\sin\sigma_z\cos\theta\sin\omega\sin\sigma \\ \sin\sigma_x\cos\theta\cos\sigma + \sin\sigma_y\sin\theta\sin\omega\sin\alpha - \\ \cos\sigma_y\sin\sigma_x\cos\omega\cos\alpha + \\ \cos\alpha_y\cos\theta_x\cos\theta\sin\omega\sin\sigma \end{pmatrix}$$

The collimator angle is obtained by $$\alpha = \cos^{-1}(G' \cdot C') = \cos^{-1}\begin{pmatrix} \cos\theta \\ 0 \\ -\sin\theta \end{pmatrix}.$$

$$\begin{pmatrix} \cos\sigma_z\cos\sigma_y\cos\theta\cos\sigma + \cos\sigma_z\cos\sigma_y\sin\theta\sin\omega\sin\alpha + \\ \cos\sigma_z\sin\sigma_y\sin\sigma_x\cos\omega\sin\sigma - \cos\sigma_x\sin\sigma_y\cos\sigma_z\cos\theta\sin\omega\sin\alpha + \\ \sin\sigma_z\cos\sigma_x\cos\omega\sin\alpha + \sin\sigma_z\sin\alpha_z\sin\theta\cos\alpha - \\ \sin\sigma_z\sin\sigma_z\cos\theta\sin\omega\sin\alpha \\ \sin\sigma_z\cos\sigma_y\cos\theta\cos\alpha + \sin\sigma_z\cos\sigma_y\sin\theta\sin\omega\sin\sigma + \\ \sin\sigma_z\sin\sigma_y\sin\sigma_x\cos\omega\sin\sigma - \sin\sigma_x\sin\sigma_y\cos\sigma_z\cos\theta\sin\omega\sin\sigma + \\ \cos\sigma_z\cos\sigma_x\cos\omega\sin\sigma - \cos\sigma_y\sin\sigma_x\sin\theta\cos\sigma + \\ \cos\sigma_x\sin\sigma_z\cos\theta\sin\omega\sin\sigma \\ \sin\sigma_y\cos\theta\cos\sigma + \sin\sigma_y\sin\theta\sin\omega\sin\alpha - \\ \cos\sigma_y\sin\sigma_x\cos\omega\sin\alpha + \cos\sigma_y\cos\sigma_z\cos\theta\sin\omega\sin\sigma \end{pmatrix}$$

$= \cos^{-1}(\cos\alpha_z\cos\sigma_y\cos^2\theta\cos\alpha + \cos\sigma_z\cos\sigma_y\sin\theta\cos\theta\sin\omega\sin\alpha + \cos\theta\cos\sigma_z\sin\sigma_y\sin\sigma_x\cos\omega\sin\alpha - \cos\sigma_x\sin\sigma_y\cos\sigma_z\cos^2\theta\sin\omega\sin\alpha - \cos\theta\sin\alpha_z\cos\sigma_x\cos\omega\sin\alpha + \sin\sigma_x\sin\sigma_z\sin\theta\cos\theta\cos\sigma -$ -continued $$\sin\sigma_z\sin\sigma_x\cos^2\theta\sin\omega\sin\alpha - \sin\theta\sin\sigma_y\cos\theta\cos\alpha -$$
$$\sin\sigma_x\sin^2\theta\sin\omega\sin\alpha + \sin\theta\cos\sigma_y\sin\sigma_x\cos\omega\sin\alpha +$$
$$\cos\sigma_y\cos\sigma_z\sin\theta\cos\theta\sin\omega\sin\alpha)$$

By using the above equation, full six-degree correction is performed to rotate the treatment beam of the patient instead of the treatment couch.

Figure 8:
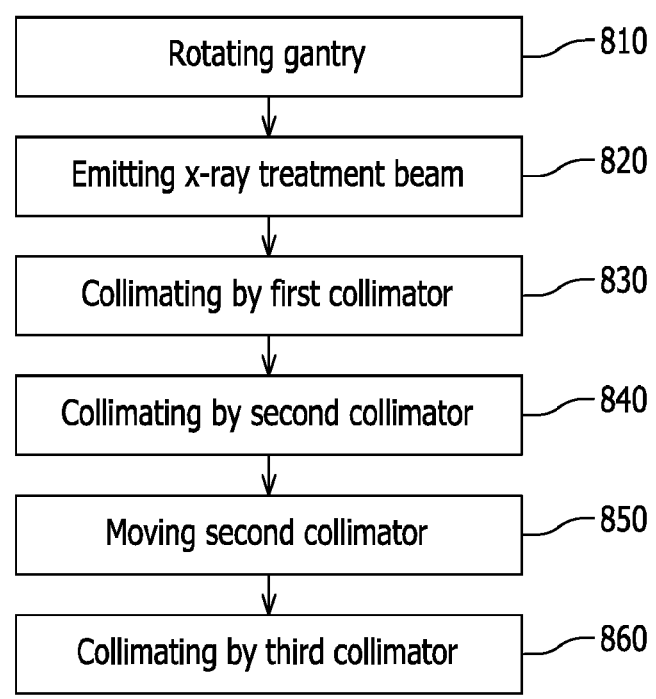
FIG. 8 illustrates a flow chart of an exemplary embodiment of the method for optimizing non-coplanar delivery without a gimbal head.

FIG. 8 illustrates a flow chart of an exemplary embodiment of the method for optimizing non-coplanar delivery without a gimbal head. In the description of the flowcharts, the functional explanation marked with numerals in angle braces, <nnn>, will refer to the flowchart blocks bearing that number.

At step <810>, the gantry 210 of FIG. 2 is rotated around the body of the patient positioned along with the longitudinal axis 280. Preferably, the control unit 205 can be operated to send a signal to the gantry 210 so that the gantry 210 starts to rotate.

At step <820>, the x-ray treatment beam is emitted from the radiation treatment source 220. The x-ray treatment beam is emitted in a direction that is traverse to the longitudinal axis 280. Preferably, the x-ray treatment beam is emitted in a direction that is substantially perpendicular to the longitudinal axis 280.

At step <830>, the x-ray treatment beam emitted by the radiation treatment source 220 is collimated by the first collimator 230. The first collimator 230 collimates the x-ray treatment beam to its maximum field size. The radiation field collimated by the first collimator is larger than a radiation field collimated by the second collimator.

At step <840>, the x-ray treatment beam collimated by the first collimator 230 is further collimated by the second collimator 240. The second collimator 240 collimates the x-ray treatment beam to a rectangular shape field that is large enough to enclose the target in the patient's body. The radiation field collimated by the second collimator is larger than a radiation field collimated by the third collimator.

At step <850>, the second collimator 240 moves out of the gantry rotation plane along the longitudinal axis 280. Preferably, the second collimator 240 is movably attached to the gantry 210.

At step <860>, the x-ray treatment beam collimated by the second collimator 240 is further collimated by the third collimator 250. The third collimator 250 collimates the x-ray treatment beam in a direction of a target in the patient's body. The third collimator 250 collimates the x-ray treatment beam to the actual shape of the radiation field. In one embodiment, the third collimator 250 is a cone collimator movably attached to a guiding rail. As described in FIG. 3, the cone collimator 320 is configured to move along the guiding rail relative to the movement of the patient such that the x-ray treatment beam follows the target while the patient moves along the longitudinal axis 280. The patient is moving with the couch 270 along the longitudinal axis 280. Preferably, the second collimator 240 and the third collimator 250 moves simultaneously during treatment.

In one embodiment, the control unit 205 can be configured to control the movement/operation of the first collimator 230, the second collimator 240, and/or the third collimator 250. In addition, the control unit 205 can also be configured to control the radio treatment source 220.

In one embodiment, a step of correcting rotation setup error of the patient can be additionally performed. In this embodiment, one or more of a gantry angle θ, non-coplanar angle ω and collimator angle α can be used to correct the rotation setup of the patient such that an orientation of the x-ray treatment beam relative to the patient remains unchanged throughout treatment as described above with reference to the calculation of the gantry angle θ, non-coplanar angle ω and collimator angle α. While this correction can be applied to the method described in FIG. 8 and the system described in FIG. 2, this step can be also performed in a robotic radiosurgery system in conjunction with a conventional linear accelerator such as a CyberKnife® machine and the system disclosed in Näfstadius.

Figure 9:
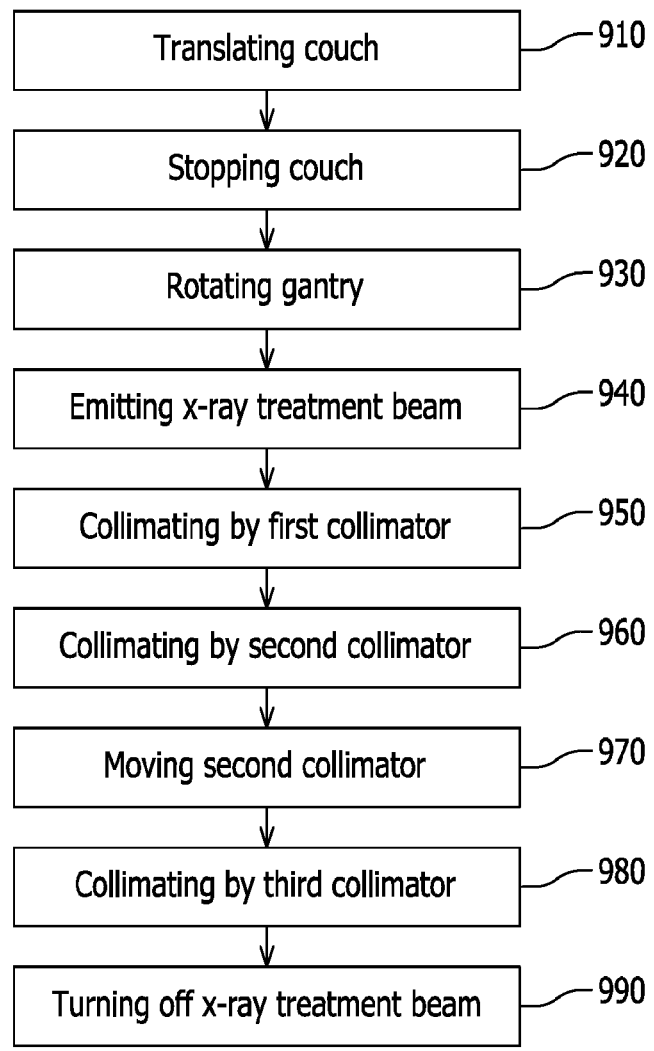
FIG. 9 illustrates a flow chart of an exemplary embodiment of the method for optimizing non-coplanar delivery without a gimbal head in a step-and-shoot delivery mode.

FIG. 9 illustrates a flow chart of an exemplary embodiment of the method for optimizing non-coplanar delivery without a gimbal head in a step-and-shoot delivery mode.

At step <910>, the couch 270 of FIG. 2 translates along the longitudinal axis 280. A patient is lying on the couch 270.

At step <920>, when the couch 270 reaches a new target position, the couch 270 is operated to stop.

Steps <930> through <980> are performed in the same manner as the steps <810> through <860> of FIG. 8.

At step <990>, the x-ray treatment beam is turned off when the gantry 210 completes a full 360 degree rotation. The couch 270 then translates to a new target position and the steps <910> through <980> are repeated. In this embodiment, the couch 270 is operated to stop at each time the gantry 210 makes a full rotation. The gantry 210 and the collimators 240 and 250 are configured to move until the gantry 210 completes its full rotation.

Figure 10:
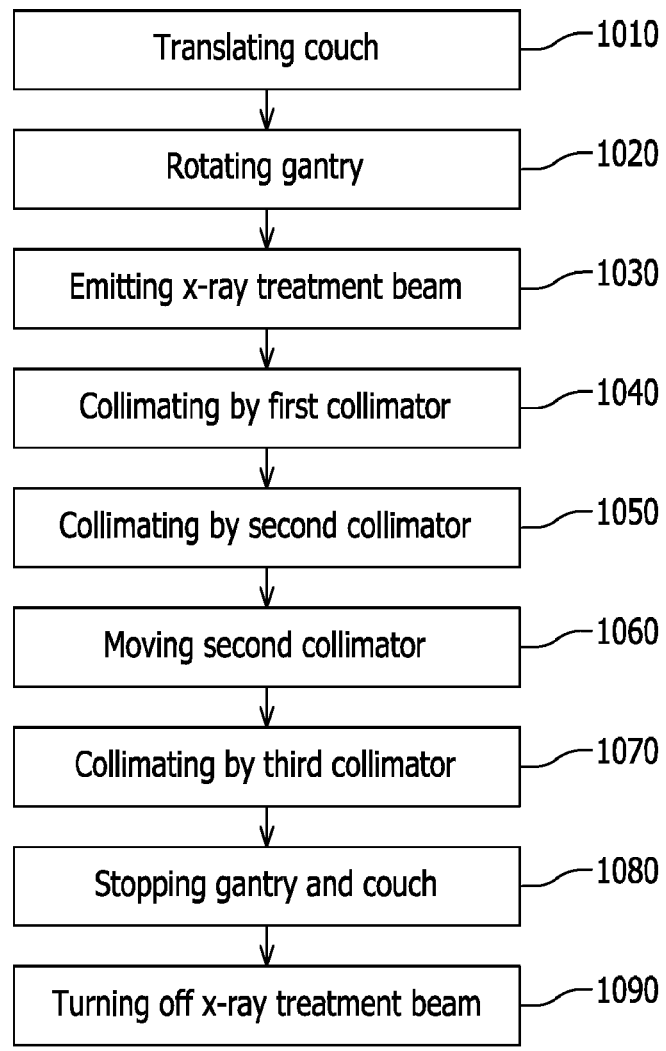
FIG. 10 illustrates a flow chart of an exemplary embodiment of the method for optimizing non-coplanar delivery without a gimbal head in a continuous helical delivery mode.

FIG. 10 illustrates a flow chart of an exemplary embodiment of the method for optimizing non-coplanar delivery without a gimbal head in a continuous helical delivery mode.

At step <1010>, the couch 270 of FIG. 2 translates along the longitudinal axis 280. A patient is lying on the couch 270.

At step <1020>, unlike the method described in FIG. 9, the gantry 210 is operated to rotate while the couch 270 is translating. Steps <1020> through <1070> are performed in the same manner as the steps <930> through <980> of FIG. 9. The gantry 210 and the collimators 240 and 250 move simultaneously during the treatment.

At step <1080>, the gantry 210 and the couch 270 are operated to stop when the couch 270 reaches a new target position.

At step <1090>, the x-ray treatment beam is turned off. In this embodiment, the x-ray treatment beam is not turned off until the treatment is completed.

In one embodiment, the control unit 205 can be configured to control the movement/operation of the first collimator 230, the second collimator 240, the third collimator 250, and/or the couch 270. In addition, the control unit 205 can also be configured to control the radio treatment source 220.

It should be understood that the above steps of FIGS. 8, 9, and 10 are illustrated in a certain order to provide an example and should not be used to limit the scope of the present invention. For example, certain steps can be performed in a different order.

It should also be understood that when introducing elements of the present invention in the claims or in the above description of the preferred embodiment of the invention, the terms "comprising", "applying", and "using," are intended to be open-ended and mean that there may be additional elements other than the listed elements. Moreover, use of identifiers such as first, second, and third should not be construed in a manner imposing time sequence between limitations unless such a time sequence is necessary to perform such limitations. Still further, the order in which the steps of any method claim that follows are presented should not be construed in a manner limiting the order in which such steps must be performed unless such order is necessary to perform such steps.

The invention claimed is:

1. A system for radiation treatment, said system comprising:
   a gantry configured to rotate around a body of a patient positioned along with a longitudinal axis;
   a radiation treatment source affixed to said gantry, wherein said radiation treatment source is configured to emit an x-ray treatment beam in a direction that is transverse to said longitudinal axis;
   a first collimator affixed to said gantry, wherein said first collimator is configured to collimate the x-ray treatment beam emitted from said radiation treatment source; and
   a second collimator movably attached to said gantry, wherein said second collimator is configured to further collimate the x-ray treatment beam collimated by said first collimator and move out of a gantry rotation plane along said longitudinal axis.

2. The system for radiation treatment according to claim 1, wherein said system further comprising a third collimator configured to further collimate the x-ray treatment beam collimated by said second collimator.

3. The system for radiation treatment according to claim 1, wherein said radiation treatment source is configured to emit the x-ray treatment beam in a direction that is substantially perpendicular to said longitudinal axis.

4. The system for radiation treatment according to claim 2, wherein said third collimator comprising:
   a guiding rail affixed to said gantry; and
   a cone collimator configured to further collimate the x-ray treatment beam collimated by said second collimator in a direction of a target in the patient's body, wherein said cone collimator is movably attached to said guiding rail and is configured to move along said guiding rail relative to the movement of the patient such that the x-ray treatment beam follows the target while the patient moves along said longitudinal axis.

5. The system for radiation treatment according to claim 2, wherein said third collimator comprising:
   a rotatable cartridge affixed to said gantry; and
   a multi-leaf collimator comprising a single layer, wherein said multi-leaf collimator is affixed to said rotatable cartridge, wherein said multi-leaf collimator is configured to further collimate the x-ray treatment beam collimated by said second collimator in a direction of a target in the patient's body, wherein said rotatable cartridge is configured to move with said multi-leaf collimator relative to the movement of the patient such that the x-ray treatment beam follows the target while the patient moves along said longitudinal axis.

6. The system for radiation treatment according to claim 1, wherein said third collimator comprising:
   a non-rotating cartridge affixed to said gantry; and
   a multi-leaf collimator comprising a plurality of layers, wherein said multi-leaf collimator is affixed to said non-rotating cartridge, wherein said multi-leaf collimator is configured to further collimate the x-ray treatment beam collimated by said second collimator in a direction of a target in the patient's body, wherein the x-ray treatment beam is collimated to follow the target while the patient moves along said longitudinal axis.

7. The system for radiation treatment according to claim 6, wherein said non-rotating cartridge is configured to translate out of said gantry rotation plane along said longitudinal axis such that said x-ray treatment beam collimated by said multi-leaf collimator follows the target while the patient moves along said longitudinal axis.

8. The system for radiation treatment according to claim 2, wherein said system further comprising:
   a control unit configured to control rotation movement of said third collimator by rotating said third collimator by a plurality of non-coplanar angles relative to said gantry rotation plane.

9. The system for radiation treatment according to claim 2, wherein a radiation field collimated by said first collimator is larger than a radiation field collimated by said second collimator, wherein said radiation field collimated by said second collimator encompasses at least a partial target volume.

10. The system for radiation treatment according to claim 9, wherein said radiation field collimated by said second collimator is larger than a radiation field collimated by said third collimator, wherein said radiation field collimated by said third collimator defines an actual shape of said radiation field collimated by said third collimator.

11. The system for radiation treatment according to claim 1, wherein said patient is caused to move by a couch that translates along said longitudinal axis.

12. The system for radiation treatment according to claim 1, wherein said radiation treatment source is one of a linear accelerator (LINAC) and co-60.

13. The system for radiation treatment according to claim 1, wherein said gantry is one of a ring gantry or c-arm gantry.

14. The system for radiation treatment according to claim 4, wherein said cone collimator comprising:
   an iris aperture with a plurality of layers, wherein said layers are configured to move coordinately in order to change an aperture size of said iris aperture at different layer levels such that an edge of each layer follows divergence of the x-ray treatment beam.

15. The system for radiation treatment according to claim 1, wherein said movement of said second collimator comprises one of rotational movement, tilting movement, and translational movement.

16. A method for radiation treatment, said method comprising:
   rotating a gantry around a body of a patient positioned along with a longitudinal axis;
   emitting an x-ray treatment beam with a radiation treatment source, wherein the x-ray treatment beam is emitted in a direction that is transverse to said longitudinal axis, wherein said radiation treatment source is affixed to said gantry;
   collimating the x-ray treatment beam with a first collimator, wherein said first collimator is affixed to said gantry;
   further collimating the x-ray treatment beam with a second collimator, wherein said second collimator is movably attached to said gantry; and
   moving said second collimator out of a gantry rotation plane along said longitudinal axis.

17. The method for radiation treatment according to claim 16, wherein said method further comprising:
   further collimating the x-ray treatment beam with a third collimator, wherein the x-ray treatment beam collimated by said second collimator is collimated in a direction of a target in the patient's body.

* * * * *